(12) United States Patent
Antonini

(10) Patent No.: US 7,728,145 B2
(45) Date of Patent: Jun. 1, 2010

(54) INDUSTRIAL METHOD FOR SEPARATION AND PURIFICATION OF FENTANYL BY REVERSE PHASE PREPARATIVE CHROMATOGRAPHY

(75) Inventor: Enrico Anthony Antonini, Edwardsville, IL (US)

(73) Assignee: Mallinckrodt Inc., Hazelwood, MO (US)

( * ) Notice: Subject to any disclaimer, the term of this patent is extended or adjusted under 35 U.S.C. 154(b) by 176 days.

(21) Appl. No.: 10/574,545

(22) PCT Filed: Oct. 22, 2004

(86) PCT No.: PCT/US2004/035386

§ 371 (c)(1),
(2), (4) Date: Apr. 5, 2006

(87) PCT Pub. No.: WO2005/044798

PCT Pub. Date: May 19, 2005

(65) Prior Publication Data

US 2007/0123710 A1 May 31, 2007

Related U.S. Application Data

(60) Provisional application No. 60/515,274, filed on Oct. 29, 2003.

(51) Int. Cl.
*C07D 211/26* (2006.01)
*C07D 211/70* (2006.01)

(52) U.S. Cl. ........................ 546/229; 546/315
(58) Field of Classification Search ................ 546/229
See application file for complete search history.

(56) References Cited

U.S. PATENT DOCUMENTS 4,234,684 A * 11/1980 Abbott et al. ............ 435/75
4,293,489 A * 10/1981 Debono .................... 530/317
4,317,903 A * 3/1982 Hofstetter ................. 536/16.5
4,336,333 A * 6/1982 Hamill et al. .............. 435/75
4,904,590 A * 2/1990 Fukuda et al. ............. 435/147
5,780,589 A * 7/1998 Lazarus et al. ............. 530/331

FOREIGN PATENT DOCUMENTS

EP 1398320 A1 * 5/2003
EP 1 398 320 3/2004

OTHER PUBLICATIONS

Lurie, Ira S.; Allen, Andrew C.; Issaq, Haleem STN Accession No. 1984:428365 , Abstract of Journal of Liquid Chromatography (1984), 7(3), 463-73.*
Lurie, I. S.; Allen, A. C. ATN Accession No. 1984:497748 Abstract of Journal of Chromatography (1984), 292(2), 283-94.*
Portier, E. J. G.; de Blok, K.; Butter, J. J.; van Boxtel, C. STN Accession No. 1999:167364; Abstract of Journal of Chromatography, B: Biomedical Sciences and Applications (1999), 723(1 + 2), 313-318.*
Hearst et. al. Proceedings of the National Academy of Sciences, USA. 1992, 89, 4514-4518.*
Practical HPLC Method Development, 2nd Edition.*
Jonczyk, et al. Przemysl Chemiczny 1978, 57, 4, 180-182 (English version is provided).*
Portier, E.J.; Abstract of Journal of Chromatography, B: Biomedical Sciences and Applications, 1999, 723 (1+ 2) 313-318.
Hearst et al.; Proceedings of the National Academy of Sciences, USA, 1992, 89, 4514-4518.
Bagley, et al., Synthesis and Analysis of the Opioid Analgesic [$^{14}$C]-Fentanyl, Journal of Labelled Compounds and Radiopharmaceuticals, vol. XXI, No. 11, pp. 945-950.

* cited by examiner

*Primary Examiner*—D. Margaret Seaman
*Assistant Examiner*—Nizal S Chandrakumar

(57) ABSTRACT

There is described a process for the purification of an impure preparation containing fentanyl by means of a reverse phase preparative chromatography process. A chromatographic column is loaded with a stationary phase, typically a silica particle having an organic ligand bound thereto. With a loading ratio of from about 50 to about 150 the impure preparation is acidified and passed through the column. The column is eluted with typically an aqueous solution of acetonitrile and the purified fentanyl is obtained in a specified cut.

21 Claims, 1 Drawing Sheet

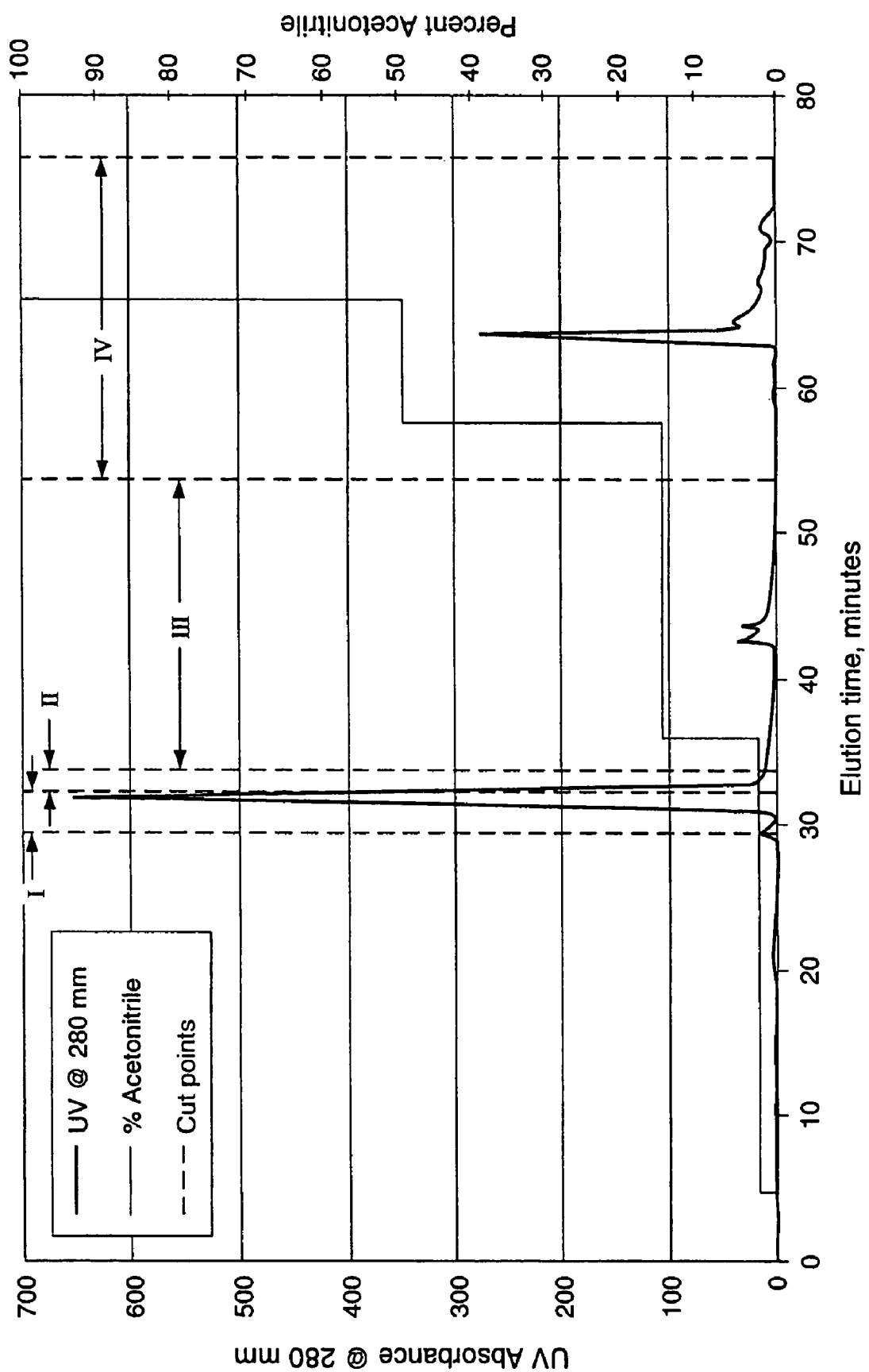

INDUSTRIAL METHOD FOR SEPARATION AND PURIFICATION OF FENTANYL BY REVERSE PHASE PREPARATIVE CHROMATOGRAPHY

CROSS REFERENCE TO RELATED APPLICATIONS

This application is a national stage application of PCT/US2004/035386, filed Oct. 22, 2004, which claims the benefit of U.S. Provisional Application No. 60/515,274 filed Oct. 29, 2003.

FIELD OF THE INVENTION

This invention relates to a method for the separation and purification of fentanyl on an industrial scale by means of reverse phase preparative chromatography. More particularly, the process of this invention provides highly pure fentanyl conveniently and in industrial quantities.

BACKGROUND OF THE INVENTION

Fentanyl is the common name for N-Phenyl-N-[1-(2phenylethyl)-4-piperidinyl]propanamide, a well-known powerful analgesic in the narcotic range and a known tranquilizer in veterinary practice. It is typically provided commercially in the form of the citrate salt also known as N-(phenethyl-4-piperdyl)propionanilide citrate.

An early process for the manufacture of fentanyl is found in U.S. Pat. No. 3,164,600 to Janssen. Following this early disclosure, precipitation and re-crystallization typically purified the product. Multiple precipitations were typically required to provide adequate purity for pharmaceutical use. In addition to yield loss in such processes, this practice greatly increases the complexity and cost of the product. Furthermore, precipitation processes can be lengthy requiring extended filtration time due to the particle size that is eventually produced.

One example of an attempt to improve the precipitation and crystallization process for pharmaceuticals such as fentanyl is disclosed in U.S. Pat. No. 6,596,206 to Lee. In this method a device for generating pharmaceutical agent particles using focused acoustic energy is disclosed. A solution of the pharmaceutical is provided in a suitable solvent into which is introduced a miscible "antisolvent" that upon admixture with the solution droplet causes the pharmaceutical agent in the droplet to precipitate. The focused acoustic energy causes a small droplet of the solution to be injected into antisolvent whereupon the pharmaceutical precipitates providing a small crystalline product. A device for accomplishing this method is also disclosed. Such method and device, while providing an improvement to the precipitation method still involves solvents, antisolvents and specialized equipment, all of which maintains the above noted disadvantages of the precipitation method for separating and purifying the pharmaceutical.

Other means to achieve separation or purification of pharmaceuticals includes adsorption processes such as the use of carbon. Another is the use of adsorption through ion exchange. Although this was done with alkaloids such as codeine and morphine, it has the limitation of requiring a low feed concentration. This is due to the need for the use of high pH flushes that can cause precipitation. Any precipitation can potentially compromise the entire purification process. Another disadvantage to this process is that significant salt is required so that another step of either dialysis or reverse osmosis is required for ion-removal.

Yet another way to achieve adsorption is through polar interaction or normal phase adsorption. Although this method is successful, it requires the extensive use of organic solvents. Moreover, although the alkaloids can be separated from each other, more evaporation is required.

Any use of analytical chromatography on narcotics such as fentanyl would guide an individual of ordinary skill in the art away from using preparative chromatography for an industrial scale process. Unlike preparative chromatography, analytical chromatography generally requires complete separation of each peak. Unlike preparative chromatography, complete separation of each peak is measured by ultraviolet (UV) absorbency. This is achieved by loading an infinitely small mass of the feed onto the column, and using a small particle size diameter (often less than 5 micrometers (196.85 microinches) in the stationary phase. The small particle size generates much higher pressures than those found in preparative chromatography. These higher pressures mandate the use of very large, strong and expensive chromatography equipment, which would negate the commercial viability for this analytical process. The equipment would also be very large in consideration that an infinitely small mass of feed is loaded in each run. In preparative chromatography, the objective is to recover the desired feed component with the required purity. The desired component can be recovered with impurities, so long as the impurities are within specification limits. The particle size of the stationary phase is small enough to achieve the separation, but is often greater than 10 microns (393.70 microinches). This limits the pressure drop generated. Also, in preparative chromatography, the maximum amount of feed is loaded with the constraint of attaining the desired product quality. This allows the product to leave the column with a maximum concentration, which then minimizes the size of the downstream equipment, especially any evaporating or concentrating units.

Various patents refer to preparative chromatography for the purpose of purifying or separating various non-ionic chemicals. Early patents in this field are U.S. Pat. No. 4,396,598 to Lin (X-ray contrast agents) and U.S. Pat. No. 5,204,005 to Doran, et al. In the '005 patent the process involves packing a chromatographic column with a chromatographic packing material, passing through the column a solution containing a water-soluble, nonionic contrast media compound and non-ionic compounds as impurities at a loading ratio between approximately 10 to 1 to 1.5 to 1 weight packing material/total weight nonionic compounds. The column is then eluted to produce an eluate containing the nonionic contrast media compound.

Numerous publications followed the above '005 patent indicating various chromatographic systems, including flash, HPLC and preparative chromatography for separating various agents but not indicating conditions, clearly not teaching any industrial process. Such publications include Published Appln. US 2003/0087306, employing various chromatographic processes for separation of multimeric agents that modulate receptors, U.S. Pat. Nos. 6,395,752 and 6,127,385 indicating isomerization of L-threo-methylphenidate, U.S. Pat. No. 4,909,941 isolating recombinant deoxyribonucleic proteins, U.S. Pat. No. 6,261,537 relating to recovery of diagnostic/therapeutic agents having microbubbles coupled to one or more vectors, U.S. Pat. No. 6,331,289 relating to targeted diagnostic/therapeutic agents having more than one different vector and Published Appln. U.S. 2002/010227 relating to diagnostic therapeutic agents.

A reference to preparative, reverse phase chromatography including a loading ratio is U.S. Pat. No. 4,317,903 disclosing the purification of lincomycin hydrochloride indicating a loading weight ratio of 18 to 1, of bonded phase silica gel to starting material. A combination of chromatographic separation followed by nanofiltration with final discoloration by ion exchange resins is described in U.S. Pat. No. 5,811,581. The material being separated in the '581 patent is described as non-ionic, water-soluble, tri- and hexa-iodinated opacifying agents useful as contrast agents in X-ray imaging. The chromatographic process is operated with a weight ratio of stationary phase to raw product loaded in the range of 20:1 to lower than 0.5:1.

As can be seen by the above review of the prior art, numerous organic materials have been separated or purified by means of the chromatographic process. However, in most instances the conditions under which the chromatographic separation was carried out was not indicated. Also, the materials separated by means of the chromatographic processes are greatly dissimilar to the present objects of this invention, i.e. the industrial scale separation and purification of fentanyl. While there are numerous references to analytical chromatographic applications for fentanyl, there is no suggestion that an industrial process could be employed under any conditions.

The current process for the purification of fentanyl utilizes two crystallizations of the hydrochloride salt and one alkaloid precipitation to attain the desired purity. While the purity requirements are attained, the recovery is low as about half of the fentanyl is lost to the mother liquor streams generated due to the solubility of the hydrochloride salt. Recycling the fentanyl in these streams is difficult due to the elevated level of impurities. There is a need for a more efficient and direct method to isolate highly pure fentanyl.

The present invention is directed to overcoming one or more of the problems set forth above. These deficiencies and shortcomings include, but are not limited to, alkaloid yield loss, tedious manual solid handling operations such as the loading and unloading of centrifuges or filters, reliance on protective equipment by the operator, extensive processing steps and potential multiple precipitation in order to achieve the requisite purity requirements.

SUMMARY OF THE INVENTION

Fentanyl is currently produced through a reaction using phenethylpiperaniline (PPA). The fentanyl produced precipitates away from the reaction liquor. The solids are then dissolved with water and enough hydrochloric acid is added to prepare a sufficiently acidic solution. The acidified solution is employed in the process of this invention.

In accordance with this invention there is provided an industrial process for recovering highly pure fentanyl from an impure, acidic, aqueous solution of fentanyl which comprises subjecting said impure fentanyl to reverse-phase preparative liquid chromatography. The chromatographic process employs a packed column containing media that have a bonded-phase attached. Through a series of collected fractions, partially recycled, the highly purified fentanyl is eluted from the column and recovered in highly yield. Fentanyl is produced in accordance with this invention with PPA impurity levels less than 0.010 weight percent in the purified product.

BRIEF DESCRIPTION OF THE DRAWINGS

The attached FIGURE is a graph indicating the results of a reverse phase, preparative HPLC procedure in accordance with this invention wherein the UV analysis of the product provides an indication of the contents of each fraction of eluant delivered from the column. The FIGURE also indicates the time; fraction cut lines of each of four fractions and the acetonitrile content of the mobile phase employed in the process.

DETAILED DESCRIPTION OF THE INVENTION

Definitions

Area %: A unit of purity calculated from analytical chromatography. It is the area of the desired component divided by the total area detected.

Loading ratio: Mass of stationary phase divided by the mass of alkaloid loaded in purification runs.

Mobile phase: The liquid that is pumped to the column after the feed is loaded. This liquid elutes the components.

Second crop: The alkaloid mass recovered in fractions that require a second pass through the chromatography column. The fractions are concentrated and then purified separately.

Stationary phase: The media that adsorbs the components of the fed to the column.

Yield: The mass of desired component recovered in purified fractions divided by the mass of component fed to the column.

Percent: Unless otherwise noted all percentage amounts stated in this specification and claims are percent by weight.

In accordance this invention, fentanyl is obtained through a reaction using phenethylpiperaniline. As noted above the precipitate from that reaction is used to prepare the mobile phase. The precipitate is first dissolved in water and the solution is acidified with an appropriate acidifying agent. Typically, the concentration of the fentanyl in the aqueous solution is in the range of from about 5 g/l to about 35 g/l and conveniently about 20 g/l. Non-limiting examples of an acids employed to acidify the fentanyl solution include, but are not limited to, inorganic acids such as hydrochloric acid, hydrobromic acid, phosphoric acid, phosphorous acid, nitric acid and sulfuric acid. Organic acids may also be employed and may typically be acetic acid, formic acid, oxalic acid, succinic acid, lactic acid and tartaric acid. The amount of acid employed is that which is sufficient to lower the pH of the fentanyl solution to a pH that is preferably in a range from about 2 to about 5 and most preferably a pH that is from about 3 to about 4. A dilute inorganic acid such as dilute hydrochloric acid is preferred since other stronger acids may degrade the fentanyl solution. The amount of acid added is to ensure that the fentanyl is converted to a salt. It has been found that the maximum retention of fentanyl is obtained when the fentanyl is fed to the column in the free base form. Thus, to ensure that the fentanyl can be recovered in a reasonable flush volume, the feed solution needs to be properly acidified. A solution containing from about 0.5 percent to about 3.5 percent fentanyl is typically prepared. Preferred solutions contain from about 1.5 to about 2.5 percent fentanyl and most preferred solutions contain about 2.0 percent fentanyl.

The stationary phase may be one of various materials from the group consisting of alkylsilanes, arylsilanes, haloalkylsilanes, alkyl esters, aryl esters, alkyl amines, alkylcyano compounds, alkyldiols, alkyl ethers, aryl ethers, haloalkyl ethers, alkylcarboxylic acids, arylcarboxylic acids, alkysulfonic acids, arylsulfonic acids, polystyrenedivinylbenzene, aminopolycaprolactem and glycidoxyethylmethoxysilzne. The stationary phase media utilized is typically silica with octyl-(C8) ligands, although other ligands such as octadecyl-(C18) and butyl-(C4) ligands may be employed. The ligands can be attached to other particles such as polymers, zirconium oxide or to titanium. The stationary phase is preferably 20 microns (787.4 microinches) spherical particles with 120 Angstroms (0.47 microinches) pores.

A high-performance preparative liquid chromatography column is generally employed. The preparative chromatography column, in an exemplary preferred system, includes a diameter that is at least about 5 centimeters (1.97 inches). The length of the preparative chromatography column is not critical to the process with a preferred length that ranges from about 5 centimeters (1.97 inches) to about 100 centimeters (39.4 inches) with a more preferred length that ranges from about 20 centimeters (7.87 inches) to about 30 centimeters (11.81 inches). Even more preferred is a column about 25 centimeters in length. There are a variety of commercial suppliers that can build preparative chromatography columns of this nature including Amicon, Inc., having a place of business at 72 Cherry Hill Drive, Beverly, Mass. 01915. Amicon, Inc. is the manufacturer of PROCHROM® chromatography columns. Other manufacturers include TechniKrom, Incorporated, having a place of business at 1801 Maple Avenue, Evanston, Ill. 60201, among others. The present invention is applicable to a wide variety of high-performance liquid preparative chromatography columns and is not limited to the specific embodiment detailed in this patent application.

Fentanyl and impurities are adsorbed onto the stationary phase and are desorbed, or eluted with a mobile phase containing dilute hydrochloric acid and an organic polar solvent. The aqueous mobile phase is prepared by acidifying water with enough hydrochloric acid to attain a pH of 2.5 to 3.5. A more preferred pH range is 2.8 to 3.2. Other acids can be used such as acetic, formic, hydrobromic, nitric and tartaric acids. The organic polar solvent is selected from any number of water soluble, non-interfering solvents such as methanol, propanol, isopropanol, butanol, t-butanol and preferably acetonitrile. Typically, the amount of solvent in the aqueous organic solvent solution is in the range of from about 2 percent to about 100 percent. Typically, the amount of organic solvent in the mobile phase increases during the elution process with lower amounts used in the first few passes of mobile phase through the column and then increased amounts are employed to purge the column.

A critical feature of this invention is the Loading Ratio. It has been found that the Loading Ratio employed in the process of this invention is typically in the range of from about 50 to about 150 grams of media per gram of fentanyl loaded into the column before the mobile phase is employed. Most typically, the Loading Ratio is in the range of from about 70 to about 130. As is well known, in the analytical use of HPLC the Loading Ratio would be above 10,000 and the feed components would elute in separate peaks. In the preparative chromatography such Loading Ratio would multiply the number of runs in a column by a factor of over 100 or cause the column to have more than 10 times larger diameter. Using the analytical loading conditions would make any new chromatography purification technique impractical. The feasible preparative application has elution fronts, in which the fentanyl is collected with the desired purity.

The desired purity obtained in the process of this invention is, of course, in some measure dependent upon the amount of impurities and operating conditions of the chromatographic process. In instances of higher impurities, a Loading Ratio in the higher level of the above noted range would be required. Also, the amount of organic solvent in the mobile phase must be controlled so as not to elute impurities prematurely. As can be seen in the operating examples below those runs with a higher total amount of elution produced higher impurities.

In operation, after the fentanyl feed solution is loaded into the packed column, the first components are eluted with a mobile phase containing from about 2 to about 10 percent, by weight, organic solvent. As noted above the preferred solvent is acetonitrile. Most of the PPA and other impurities are collected in a first fraction and is discarded. A second fraction is collected containing an initial, small amount of fentanyl and the remaining PPA. The second crop will contain about 10 percent of the fentanyl loaded. The purified fentanyl is then collected in the third fraction wherein the mobile phase is changed to an increased amount of solvent, in the range of about 8-10 percent, although in some instances the amount of organic solvent in the third fraction can be as high as 15 percent. The third fraction contains about 90 percent of the fentanyl loaded into the column. This third fraction is evaporated to remove the solvent and the purified alkaloid is recovered from solution by precipitation in accordance with standard procedures. A fourth fraction is then obtained to flush the column of the remaining fentanyl loaded. In the fourth fraction, the aqueous mobile phase employed contains about 50 percent organic solvent, typically acetonitrile. This fourth fraction is then combined with the second fraction and subjected to evaporation to remove the organic solvent. The combined fractions are subjected to the preparative, reverse phase preparative chromatography as described above except that no recycle fractions are collected in order to purge the impurities. The purified, combined second crop is then sent to the alkaloid precipitation procedure as noted above with respect to the third fraction.

The reverse phase, preparative chromatographic process of this invention is typically operated at a temperature of from about 20° C. to about 30° C. while higher or lower temperatures may be employed without significant change in result.

DESCRIPTION OF THE PREFERRED EMBODIMENTS

In operation, it is typical to employ UV analysis of the eluted material from the column. From this analysis a large peak is observed indicating the impurity PPA during the initial time of elution. A smaller peak is observed indicating the impurity PPA during the second fraction. A large peak is observed during the fourth fraction at which time the column is being flushed with a high concentration of organic solvent. A typical UV profile of eluted material in accordance with the process of this invention appears in the FIGURE. The process producing the UV curve in the FIGURE employed a feed solution of fentanyl hydrochloride salt at pH 3.0 to a chromatographic column having a dimension of 1×25-cm, with 15/30-micron particles of silicon having a C8 ligand attached. The Load Ratio was 100 and the flow rate was 3 ml/min. In the FIGURE, the abscissa denotes elution time in minutes while the left ordinate denotes UV absorbance at 280 nm. The right ordinate denotes percent acetonitrile in volume percent in the feed solution. The various fractions collected are denoted as I-IV on the chart.

A series of runs were performed to demonstrate the recovery and purity attained with the preparative, reverse phase, preparative chromatography purification of fentanyl. All runs used a column packed with 20-micron silica containing C8 ligands and providing 120 angstroms pores. The mobile phase consisted of water with HCl added to attain a pH of 2.8-3.2 with increasing acetonitrile. The results obtained in these runs are set forth in Table I below

TABLE I

| | | Purified Fentanyl Fraction | | | | | Second Fraction | | |
|---|---|---|---|---|---|---|---|---|---|
| Run | Load Ratio | Area % | % Yield | g/l Fent. | PPA % | % ACN | Area % | PPA % | % Yield |
| 1 | 103 | 99.88 | 87 | 1.32 | 0.006 | 9.4 | 95.64 | 0.14 | 13 |
| 2 | 88 | 99.89 | 91 | 1.56 | 0.007 | 9.6 | 51.75 | 9.15 | 9 |
| 3 | 104 | 99.86 | 70 | 0.94 | 0.010 | 10.9 | 97.65 | 0.03 | 26 |
| 4 | 131 | 99.71 | 90 | 1.07 | 0.011 | 11.2 | 51.63 | 7.10 | 10 |
| 5 | 64 | 98.65 | 86 | 1.15 | 0.014 | 11.1 | 57.52 | 5.48 | 14 |
| 6 | 50 | 98.48 | 86 | 1.43 | 0.029 | 10.8 | 48.91 | 5.63 | 14 |
| 7 | 232 | 90.02 | 86 | 0.42 | 0.106 | 13.3 | 36.78 | 7.96 | 13 |

Example 1

Two chromatographic runs were made employing the following conditions:
Objective: Recover fentanyl with less than 0.010 percent PPA
Feed Composition: 91.2 area % fentanyl, 8.6 area % (0.91 weight %) PPA
Feed pH: 3.03 with hydrochloric acid
Feed concentration: 19-g/l fentanyl
Stationary phase: silica with C8 ligands, 20 microns spherical particles with 120-angstrom pores.
Column: 1.0-cm diameter, 25-cm length, and 10.2 g of stationary phase
Flow Rate: 3 ml/min.
Flow direction: top to bottom
Temperature: 25° C.
Detection: 280 nm.
Mobile Phase: dilute hydrochloric acid solution in water at pH 3.12 and acetonitrile (ACN) added in step gradients of 2.5 to 100 volume percent.
The results of the two runs appear in Table II below.

TABLE II

| | RUN 1 | RUN 2 |
|---|---|---|
| Loading Ratio | 103 | 50 |
| Area % fentanyl in purified fraction | 99.88 | 98.48 |
| Percent PPA in purified fraction | 0.006 | 0.029 |
| Yield of fentanyl in purified fraction | 87 | 86 |
| Elution prior to fentanyl elution | 27.3 ml of aqueous 66.5 ml of 2.5% ACN | 69 ml of aqueous 45 ml of 5% ACN |
| Elution of fentanyl-PPA fraction | 5.3 ml of 2.5% ACN | 10.8 ml of 5% ACN |
| Elution of purified fraction | 27.5 ml of 2.5% ACN 34.0 ml of 15% ACN | 26.7 ml of 5% ACN 40.5 ml of 10% ACN 44.5 ml of 15% ACN |
| Elution of late-eluting fentanyl fraction | 22.1 ml of 15% ACN 32.5 ml of 50% ACN 11 ml of 100% ACN | 28.5 ml of 50% ACN 15 ml of 95% ACN |

In Run 1 the PPA was reduced to less than 0.01 weight percent, which did not occur in Run 2 of Table 2. Run 1 used a loading ratio of 103 while Run 2 of Table 2 loaded too much feed at a ratio of 50. The separation of fentanyl and PPA was aided in Run 1 by using an initial acetonitrile flush of 2.5 volume percent. Run 2 used a higher initial acetonitrile flush of 5 volume percent and this made separating the PPA and fentanyl more difficult. Both runs had nearly the same recovery of fentanyl in the purified fraction, and the remaining fentanyl was recovered in the fentanyl-PPA and late-eluting fractions. These fractions were designated as second crop and were to be purified a second time through the column.

Example 2

Another pair of runs was made to demonstrate the need to attain the proper Loading Ratio in the process of this invention. The operating conditions described above with respect to Example 1 were employed in this example. The results of the runs are contained in Table III below.

TABLE III

| | RUN 3 | RUN 4 |
|---|---|---|
| Loading Ratio | 88 | 64 |
| Area % of fentanyl in purified fraction | 99.89 | 98.65 |
| Weight % of PPA in purified fraction | 0.007 | 0.014 |
| Yield of fentanyl in purified fraction | 91 | 86 |
| Elution prior to fentanyl elution | 27.5 ml of aqueous 45.0 ml of 5% ACN | 31 ml of aqueous 71.8 ml of 5% ACN |
| Elution of fentanyl-PPA fraction | 8.6 ml 5% ACN | 6.7 ml of 5% ACN |
| Elution of purified fraction | 36.2 ml of 5% ACN 31.0 ml of 15% ACN | 24.1 ml of 5% ACN 38.5 ml of 10% ACN 49.0 ml of 15% ACN |
| Elution of late-eluting fentanyl fraction | 27 ml of 15% ACN 36.5 ml of 50% ACN 9.0 ml of 100% ACN | 39.5 ml of 50% ACN |

In Table III, Run 3 demonstrated the desired reduction of the PPA impurity. The PPA level in Run 4 was slightly above the desired 0.01 percent. The higher amount of impurity in Run 4 of Table III is due in most part to using a Loading Ratio of 64 compared to 88 for Run 3. Run 3 used less elution volume than Run 4 to collect the purified fentanyl. This was because Run 3 omitted the flush of 10% acetonitrile. It is clear from the data in Table III that a higher Loading Ratio is required for the amount of impurity in the feed as well as to compensate for other operating conditions. The use of a slightly larger fentanyl-PPA fraction volume in Run 3 also aided in the reduction of PPA.

There has been described a novel process for the preparation of fentanyl by means of reverse phase, preparative chromatography. While the process of this invention has been described with reference to specific compounds and examples, no intention is made by such reference to limit the scope of this invention unless expressly stated. Various modifications may be made in the materials and sequence of process steps as well as process combinations, which are adapted to suit the various process steps without departing from this invention. The foregoing description is given for clarity of understanding only and no unnecessary limitations should be understood there from, as modifications will be obvious to those skilled in the art.

What is claimed is:

1. An industrial process for recovering pure fentanyl from an impure aqueous preparation comprising fentanyl containing phenethylpiperaniline, the process comprising:
    subjecting said impure aqueous preparation to a reverse-phase high performance preparative liquid column chromatography, the column containing a stationary phase, the stationary phase being bonded-phase silica containing ligands selected from the group consisting of butyl-, octyl- and octadecyl-moieties, the chromatography comprising contacting the column with the aqueous preparation and then eluting the column with a mobile phase comprising an aqueous acidic solution containing an organic solvent, the aqueous mobile phase pH being in the range of from about 2.5 to about 3.5, and
    recovering pure fentanyl,
    wherein the pure fentanyl comprises a phenethylpiperaniline impurity level of less than about 0.010 weight percent, and further wherein a loading ratio of column media to fentanyl loaded onto the column is in the range of from about 50 to about 150.

2. The process of claim 1 wherein the loading ratio is in the range of from about 70 to about 130.

3. The process of claim 1 wherein the ligand is octyl-silane.

4. The process of claim 1 wherein the acid employed to acidify the aqueous mobile phase is selected from the group consisting of acetic, formic, tartaric, hydrobromic, nitric and hydrochloric acid.

5. The process of claim 1 wherein the pH of the aqueous mobile phase is in the range of from about 2.8 to about 3.2.

6. The process of claim 1 wherein the organic solvent is an alcohol.

7. The process of claim 6 wherein the alcohol is selected from the group consisting of methanol, propanol, isopropanol, butanol and t-butanol.

8. The process of claim 1 wherein the organic solvent is acetonitrile.

9. The process of claim 1 wherein the impure preparation is acidified so as to prepare a fentanyl salt.

10. The process of claim 9 wherein the acid employed to acidify the aqueous solution of fentanyl is an inorganic acid.

11. The process of claim 10 wherein the acid is selected from the group consisting of hydrochloric acid, hydrobromic acid, phosphoric acid, phosphorous acid, sulfuric acid and nitric acid.

12. The process of claim 9 wherein the acid employed to acidify the aqueous solution of fentanyl is an organic acid.

13. The process of claim 12 wherein the organic acid is selected from the group consisting of acetic acid, formic acid, oxalic acid, succinic acid, lactic acid and tartaric acid.

14. The process of claim 9 wherein the pH of the aqueous solution of fentanyl is in the range of from about 2 to about 5.

15. The process of claim 14 wherein the pH of the aqueous solution of fentanyl is in the range of about from about 2.5 to about 3.5.

16. The process of claim 11 wherein the acid is hydrochloric acid.

17. The process of claim 8 wherein the concentration of acetonitrile in the aqueous mobile phase is in the range of from about 2 to about 100 volume percent.

18. The process of claim 8 wherein the concentration of acetonitrile in the aqueous mobile phase is in the range of from about 5 to about 10 volume percent during the collection of the purified fentanyl.

19. A process for purifying an impure preparation of fentanyl containing phenethylpiperaniline which comprises the steps of:
    (a) packing a preparative chromatographic column with a reverse-phase chromatographic packing material comprising bonded-phase silica containing ligands selected from the group consisting of butyl-, octyl- and octadecyl-moieties;
    (b) passing through said column an aqueous, acidified solution of impure fentanyl at a loading ratio of from about 50 to about 150; and
    (c) eluting said column with an aqueous acidic solution of an organic solvent with a pH in the range of from about 2.5 to about 3.5 to produce an eluate containing fentanyl having less than about 0.010 weight percent phenethylpiperaniline.

20. The process of claim 19 wherein the eluate is divided into four cuts wherein:
    (i.) a first cut is discarded,
    (ii.) a second cut that is combined with a fourth cut wherein the aqueous solution of an organic solvent is reduced and then recycled through the column, and
    (iii.) a third cut that contains less than about 0.010 percent phenethylpiperaniline.

21. An industrial process for recovering pure fentanyl from an impure aqueous preparation comprising fentanyl containing phenethylpiperaniline, the process comprising:
    acidifying the impure aqueous preparation to prepare a fentanyl salt with a pH in the range of from about 2.5 to about 3.5;
    subjecting said impure aqueous preparation to a reverse-phase high performance preparative liquid column chromatography, the column containing a stationary phase, the stationary phase being bonded-phase silica containing ligands with octyl-moieties, the chromatography comprising contacting the column with the aqueous preparation and then eluting the column with a mobile phase comprising an aqueous acidic solution containing an organic solvent, the aqueous mobile phase pH being in the range of from about 2.5 to about 3.5, and
    recovering pure fentanyl,
    wherein the pure fentanyl comprises a phenethylpiperaniline impurity level of less than about 0.010 weight percent, and further wherein a loading ratio of column media to fentanyl loaded onto the column is in the range of from about 50 to about 150.

* * * * *